United States Patent
Burkard et al.

(10) Patent No.: US 6,706,193 B1
(45) Date of Patent: Mar. 16, 2004

(54) METHOD FOR RECOVERING FLUORINATED EMULSIFIERS FROM AQUEOUS PHASES

(75) Inventors: Georg Burkard, Altötting (DE); Klaus Hintzer, Kastl (DE); Gernot Löhr, Burgkirchen (DE)

(73) Assignee: 3M Innovative Properties Company, St. Paul, MN (US)

( * ) Notice: Subject to any disclaimer, the term of this patent is extended or adjusted under 35 U.S.C. 154(b) by 36 days.

(21) Appl. No.: 10/009,757

(22) PCT Filed: Jul. 11, 2000

(86) PCT No.: PCT/EP00/06556

§ 371 (c)(1),
(2), (4) Date: Dec. 11, 2001

(87) PCT Pub. No.: WO01/05710

PCT Pub. Date: Jan. 25, 2001

(30) Foreign Application Priority Data

Jul. 17, 1999 (DE) .......................................... 199 33 696

(51) Int. Cl.⁷ ............................. C02F 1/42; B01D 17/12
(52) U.S. Cl. ...................... 210/662; 210/639; 210/663; 210/669; 210/683; 210/702; 523/310; 523/332; 528/482; 560/227; 562/605; 562/608
(58) Field of Search .................................. 210/638, 639, 210/644, 649, 662, 663, 669, 683, 691, 702, 806, 915; 252/302, 315.4; 554/177; 562/605, 608; 510/315.1; 560/227; 523/310, 332; 528/482

(56) References Cited

U.S. PATENT DOCUMENTS

| 3,882,153 | A | | 5/1975 | Sekr et al. | |
| 4,282,162 | A | | 8/1981 | Kuhls | |
| 4,369,266 | A | | 1/1983 | Kuhls et al. | ................. 523/332 |
| 5,017,480 | A | * | 5/1991 | Mori et al. | ................. 435/106 |
| 5,312,935 | A | * | 5/1994 | Mayer et al. | ................. 554/182 |
| 5,442,097 | A | | 8/1995 | Obermeier et al. | ......... 560/227 |
| 6,518,442 | B1 | * | 2/2003 | Felix et al. | ................. 562/605 |
| 6,613,941 | B1 | * | 9/2003 | Felix et al. | ................. 562/605 |

FOREIGN PATENT DOCUMENTS

| DE | A 20 44 986 | 5/1975 |
| WO | WO 99/62830 | 12/1999 |
| WO | WO 99/62858 | 12/1999 |

OTHER PUBLICATIONS

*Encyclopedia of Polymer Science and Engineering*, vol. 7, Wiley Interscience, New York, p. 211 (1987).

* cited by examiner

*Primary Examiner*—Joseph W. Drodge
(74) *Attorney, Agent, or Firm*—James V. Lilly; Brian E. Szymanski

(57) ABSTRACT

Fluorinated emulsifiers can be recovered from an aqueous phase containing small amounts of fluoropolymer particles by treating the aqueous phase with a small amount of a nonionic surface-active agent, bringing the aqueous phase adjusted in this way into contact with an anionic exchanger resin, and liberating the adsorbed emulsifier from the exchanger resin. The finely divided fluoropolymer can be precipitated quantitatively in the untreated aqueous phase or the eluate using flocculating agents.

8 Claims, No Drawings

METHOD FOR RECOVERING FLUORINATED EMULSIFIERS FROM AQUEOUS PHASES

This application is a 371 national stage application of published PCT Application No. WO 01/05710 filed on Jul. 11, 2000, which claims priority to German Application No. 199 33 696.2, filed on Jul. 17, 1999.

DESCRIPTION

The invention relates to the work-up of waste water, in particular lightly contaminated waste water, containing fluorinated emulsifiers, as employed in the polymerization of fluorinated monomers since they do not have telogenic properties. In particular, the salts, preferably the alkali metal or ammonium salts, of perfluorinated or partially fluorinated alkanecarboxylic acids or sulfonic acids are used. These compounds are prepared by electrofluorination or by telomerization of fluorinated monomers, which is associated with considerable effort. There has therefore been no lack of attempts to recover these valuable materials from waste water.

U.S. Pat. No. 5,442,097 discloses a process for the recovery of fluorinated carboxylic acids in usable form from contaminated starting materials, in which the fluorinated carboxylic acid is, if necessary, liberated from these materials in aqueous medium using a sufficiently strong acid, the fluorinated carboxylic acid is reacted with a suitable alcohol, and the ester formed is distilled off. The starting material used here can be a polymerization liquor, in particular from emulsion polymerization, in which the fluoropolymer is prepared in the form of colloidal particles with the aid of relatively large amounts of emulsifier. "Polymerization liquor" here is taken to mean the waste water produced on isolation of the fluoropolymer by coagulation (without further process steps, such as washing). This process has proven highly successful, but requires a certain concentration of fluorinated carboxylic acid in the starting material.

The recovery of fluorinated carboxylic acids by distillation can also be carried out in the absence of alcohols. In this process variant, the fluorocarboxylic acid is distilled off in the form of a highly concentrated azeotrope. However, this process variant is industrially disadvantageous for energetic reasons. In addition, the resultant waste water is more highly contaminated than before the treatment.

DE-A-20 44 986 discloses a process for the isolation of perfluorocarboxylic acids from dilute solution in which the dilute solution of the perfluorocarboxylic acids is brought into adsorption contact with a weakly basic anion exchanger resin, and the perfluorocarboxylic acid present in the solution is thereby adsorbed onto the anion exchanger resin, the anion exchanger resin is eluted with an aqueous ammonia solution and the adsorbed perfluorocarboxylic acid is thus transferred into the eluent, and finally the acid is isolated from the eluate. However, complete elution requires relatively large amounts of dilute ammonia solution, and in addition this process is very time-consuming. These disadvantages are overcome by the process disclosed in U.S. Pat. No. 4,282,162 for the elution of fluorinated emulsifier acids adsorbed onto anion exchangers, in which the elution of the adsorbed fluorinated emulsifier acid from the anion exchanger is carried out using a mixture of dilute mineral acid and an organic solvent. In this process, the use of the acid simultaneously effects regeneration of the exchanger resin.

The use of anion exchanger resins in waste water treatment on an industrial scale is essentially hindered by the presence of fluoropolymer latex particles. The latex particles are anionically stabilized and are consequently coagulated in the anion exchanger resin. The exchanger column thus becomes blocked.

This difficulty is overcome by a proposed process for the isolation of fluorinated emulsifier resins in which the finely divided solids in the waste water are stabilized using a surfactant or a surface-active substance, and subsequently the fluorinated emulsifier acids are bound to an anion exchanger resin, and the fluorinated emulsifier acids are eluted therefrom (WO-A-99/62830). In the examples, nonionic surfactants are employed in a concentration of from 100 to 400 mg/l.

A process has now been found for the recovery of fluorinated emulsifiers from an aqueous phase, where this aqueous phase, besides the emulsifier, contains small amounts of fluoropolymer particles and possibly further substances, where an upper concentration value of a nonionic surface-active substance is determined below which no further decrease in desorption of the emulsifier bound to an anion exchanger takes place, the aqueous phase is adjusted to a concentration of nonionic surface-active agent of between the upper concentration value determined in this way and a lower concentration which is still effective for preventing coagulation of the polymer particles, the aqueous phase adjusted in this way is brought into contact with an anionic exchanger resin in order to effect the adsorption of the emulsifier onto the exchanger resin, and the emulsifier is liberated from the exchanger resin.

The suitable concentration of nonionic surface-active agent is dependent on the type of polymer, on the surface-active agent and on any other substances present in the aqueous phase. It is therefore advisable to determine the suitable concentration limits of the nonionic surface-active agent for each waste water to be treated. A maximum concentration of 10 ppm, in most cases a concentration in the range from 5 to 0.1 ppm, is usually sufficient.

Since—as mentioned above—the waste water to be treated in accordance with the invention is preferably slightly contaminated, it is sensible to add only sufficient auxiliary chemicals to the waste water as is necessary in order to avoid causing fresh contamination for the further work-up of the waste water. If, on the other hand, it is desired to avoid the respective determination of the limit values in industrial practice, where mixtures of different waste water may have to be worked up together, a mean value of about 3 ppm can generally be used without problems.

A further advantage of the use of small amounts of nonionic surface-active agent, besides avoiding unnecessary costs, is also the suppression of foam, which can be very troublesome on an industrial scale and in some cases requires further contamination of the waste water with foam suppressors.

In the preparation of fluoropolymers, such as polytetrafluoroethylene, fluorinated thermoplastics and fluorinated elastomers, the polymers are separated off by coagulation, which is carried out mechanically with high shear ratios or chemically by precipitation with mineral acids or inorganic salts. The coagulated fluoropolymers are usually agglomerated and washed with water. Relatively large amounts of process waste water thus arise, namely usually from about 5 to 10 tonnes of waste water per tonne of fluoropolymer. In these process steps, the majority of the fluorinated emulsifier is washed out and is thus present in the waste water. The concentration is usually a few millimoles per liter, corresponding to approximately 1000 ppm. Besides the constituents already mentioned above, the waste water furthermore contains chemicals from the polymerization, such as initiators and buffers, which are present in approximately the same order of magnitude as the emulsifier, and very small amounts of fluoropolymer latex particles which have not been coagulated. The proportion of these latex particles in the waste water is usually less than 0.5% by weight.

It has already been mentioned that the preparation of fluorinated emulsifiers is associated with considerable effort, especially since these substances have to be employed in high purity. Furthermore, these emulsifiers have poor biodegradability, and therefore the most complete removal possible from the waste water appears necessary. The process according to the invention allows virtually quantitative recovery, even from the slightly contaminated types of waste water defined above.

A further advantage of the low concentrations of nonionic surface-active agent is the more effective separation of the latex particles from the anion-exchanged waste water. These particles are advantageously coagulated with small amounts of organic flocculating agents, it having been found that the amount of flocculating agent required increases with increasing concentration of nonionic surface-active agent. The resultant fluoropolymers, which are now contaminated with small amounts of surface-active agent and flocculating agent, can be used in building materials and therefore do not have to be subjected to complex work-up or disposed of to landfill.

Suitable nonionic surface-active agents are the commercially available oxyethylates and oxypropylates of organic hydroxyl compounds, preference being given to non-aromatic oxyalkylates for environmental protection reasons. Preference is therefore given to oxyethylates of long-chain alcohols.

Organic flocculating agents are described, for example, in Encycl. Polym. Sci. Engng., Wiley Interscience, New York 7, 211 (1987).

The organic flocculating agents are advantageously cationic products, for example polydiallyldimethylammonium chloride.

Cationic surfactants, such as, for example, didecyidimethylatnmonium chloride, can likewise be used for precipitation of the nonionic stabilized latex particles. However, their use on an industrial scale is problematic since charge reversal of the particles to give cationically stabilized latex particles can take place preferentially if the precipitation is carried out incorrectly. This considerably reduces the degree of precipitation.

The invention is explained in greater detail in the examples below.

EXAMPLES

In the examples below, waste water of mechanically coagulated polymer dispersions comprising about 90% by weight of the perfluorooctanoic acid employed in the polymerization as well as latex particles were employed. They are not diluted with washing water from the agglomerated resins. Waste water from the polymerization of tetrafluoroethylene with ethylene, polyfluoro(n-propyl vinyl) ether, hexafluoropropene and a terpolymer of tetrafluoroethylene, hexafluoropropene and vinylidene fluoride, and mixtures of such waste water, was investigated. Since it was found that waste water of said terpolymers and of the copolymers of tetrafluoroethylene and said ether and of ethylene tended to result in blockage of the exchanger column, this waste water was investigated in greater detail.

The dimensions of the anion exchanger column were as follows: height 5 cm, diameter 4 cm, fill amount 500 ml, flow rate from 0.5 to 1 l/h, working procedure: from top to bottom. A commercially available, strongly basic anion exchanger ®AMPERLITE IRA 402, capacity 1.2 mmol/ml, was employed.

Blockage of the column was noted by monitoring the flow rate under a constant hydrostatic pressure. The experiments were carried out until the perfluorooctanoic acid appeared. A typical experiment on a laboratory scale required an amount of up to 150 l. The flow rate was determined at the beginning and at the end by weighing the exchanged waste water for a given time. A decrease in the flow rate of <20% at the end of the experiment was regarded as acceptable. At the beginning of the experiment, the anion exchanger resin was in the OH⁻ form. The determination limit for the perfluorooctanoic acid was 5 ppm.

Example 1

A process waste water ("polymerization liquor") from the polymerization of the terpolymer of tetrafluoroethylene, hexafluoropropene and vinylidene fluoride containing 0.3% by weight of polymer latex particles and 0.1% by weight of perfluorooctanoic acid was employed. A commercially available p-octylphenol oxyethylate ®TRITON X 100 (Rohm & Haas, CAS No. 9002-93-1) was employed.

TABLE 1

| Concentration of ® TRITON [ppm] | 50 | 10 | 3 | 0.3 |
|---|---|---|---|---|
| Total amount of waste water passed through [l] | 125 | 150 | 150 | 150 |
| Flow rate [l/h] | | | | |
| at the beginning | 1.0 | 1.0 | 1.0 | 1.0 |
| at the end | 0.9 | 0.95 | 1.0 | 1.0 |
| Concentration of perfluorooctanoic acid [ppm] after | | | | |
| 50 l | | <5 | <5 | <5 | <5 |
| 100 l | | 32 | 20 | <5 | <5 |
| 125 l | | >100 | 17 | 11 | 7 |
| 150 l | | — | >100 | >100 | >100 |

The perfluorooctanoic acid concentrations close to breakthrough exhibit "run-out" at relatively high concentrations of the nonionic surface-active agent. The nominal ion exchange capacity appears to be reduced at relatively high concentrations of nonionic surface-active agent.

Example 2

Example 1 is repeated with the modification that the nonionic surface-active agent employed was a commercially available fatty alcohol polyglycol ether ®GENAPOL X 080 (Hoechst AG).

TABLE 2

| Concentration of ® GENAPOL [ppm] | 300 | 30 | 3 | 0.3 |
|---|---|---|---|---|
| Total amount of waste water passed through [l] | 125 | 125 | 150 | 150 |

TABLE 2-continued

| Flow rate [l/h] | | | | |
|---|---|---|---|---|
| at the beginning | 1.0 | 1.0 | 1.0 | 1.0 |
| at the end | 0.9 | 0.9 | 0.95 | 0.95 |
| Concentration of perfluorooctanoic acid [ppm] after | | | | |
| 50 l | <5 | <5 | <5 | <5 |
| 100 l | 23 | 18 | <5 | <5 |
| 125 l | >100 | >100 | 12 | 8 |
| 150 l | — | — | >100 | >100 |

Example 3

Example 2 was repeated, but a process water ("polymerization liquor") from the polymerization of a copolymer of tetrafluoroethylene with perfluoro(n-propyl vinyl) ether containing 0.1% by weight of perfluorooctanoic acid and 0.4% by weight of polymer latex particles was employed.

TABLE 3

| Concentration of ® GENAPOL [ppm] | 30 | 3 | 0.3 |
|---|---|---|---|
| Total amount of waste water passed through [l] | 150 | 150 | 150 |
| Flow rate [l/h] | | | |
| at the beginning | 1.0 | 1.0 | 1.0 |
| at the end | 0.9 | 1.0 | 0.9 |
| Concentration of perfluorooctanoic acid [ppm] after | | | |
| 50 l | <5 | <5 | <5 |
| 100 l | <5 | <5 | <5 |
| 125 l | 15 | 7 | 9 |
| 150 l | >100 | >100 | >100 |

Example 4

Example 2 was repeated, but a process water ("polymerization liquor") from the polymerization of a copolymer of tetrafluoroethylene with ethylene containing 0.2% by weight of perfluorooctanoic acid and 0.6% by weight of polymer latex particles was employed.

TABLE 4

| Concentration of ® GENAPOL [ppm] | 30 | 3 | 0.3 |
|---|---|---|---|
| Total amount of waste water passed through | 75 | 75 | 75 |
| Flow rate [l/h] | | | |
| at the beginning | 0.5 | 0.5 | 0.5 |
| at the end | 0.45 | 0.45 | 0.45 |
| Concentration of perfluorooctanoic acid [ppm] after | | | |
| 50 l | <5 | <5 | <5 |
| 100 l | <5 | <5 | <5 |
| 125 l | 35 | 12 | 10 |
| 150 l | >100 | >100 | >100 |

Example 5

The types of waste water indicated in Tables 5 and 6 were treated with the commercially available organic flocculating agent ®MAGNOFLOC 1697 (polydiallyldimethylammonium chloride, Allied Colloids Company). The minimum concentration of the flocculating agent for quantitative precipitation of the latex particles was determined by titration. A 0.1% strength by weight solution of the flocculating agent was added dropwise to the exchanger eluate with gentle stirring. The latex particles are precipitated virtually instantaneously and settle very quickly. The dropwise addition is terminated when no further precipitate is observed. The results are shown in the following table.

TABLE 5

PFOA-free process waste water (PFOA concentration <5 ppm)

| Waste water from | Example 1 | | | Example 3 | | | Example 4 | | |
|---|---|---|---|---|---|---|---|---|---|
| ® GENAPOL concentration [ppm] | 300 | 30 | 3 | 300 | 30 | 3 | 300 | 30 | 3 |
| Minimum concentration of flocculating agent [ppm] | 23 | 3.5 | 2.6 | 27 | 3.0 | 2.7 | 35 | 9 | 7.7 |

TABLE 6

Untreated process waste water (PFOA concentration about 1000 ppm)

| Waste water from | Example 1 | | | Example 3 | | | Example 4 | | |
|---|---|---|---|---|---|---|---|---|---|
| ® GENAPOL concentration [ppm] | — | 3 | 30 | — | 3 | 30 | — | 3 | 30 |
| Minimum concentration of flocculating agent [ppm] | 4.6 | 6 | 10 | 8.3 | 10 | 15 | 8.0 | 10 | 13 |

What is claimed is:

1. A process for the recovery of fluorinated emulsifiers from an aqueous phase which, besides the emulsifier, contains small amounts of fluoropolymer particles, the process comprising;
   (a) determining desorption of the fluorinated emulsifier bound to an anion exchanger;
   (b) determining an upper concentration value of a nonionic surface-active substance below which no further decrease in desorption of the emulsifier bound to the anion exchanger takes place,
   (c) adjusting the aqueous phase to a concentration of nonionic surface-active agent of between the upper concentration value determined in this way and a lower concentration which is effective for preventing coagulation of the polymer particles,
   (d) contacting the aqueous phase with an anionic exchanger resin in order to effect the adsorption of the emulsifier onto the exchanger resin, and
   (e) liberating the emulsifier is liberated from the exchanger resin.

2. A process for the recovery of fluorinated emulsifiers from an aqueous phase which, besides the emulsifier, contains small amounts of fluoropolymer particles, wherein the aqueous phase is adjusted to a concentration of nonionic surface-active agent of between 10 ppm and a lower concentration which is effective for preventing coagulation of the polymer particles, the aqueous phase adjusted in this way is brought into contact with an anionic exchanger resin in order to effect the adsorption of the emulsifier onto the exchanger resin, and the emulsifier is liberated from the exchanger resin.

3. The process as claimed in claim 2, where the concentration of the nonionic surface-active agent is from 5 to 0.1 ppm.

4. The process as claimed in claim 1, wherein the nonionic surface-active agent is non-aromatic.

5. The process as claimed in claim 1, where the nonionic surface-active agent is a fatty alcohol oxyethylate.

6. The process as claimed claim 1, where an effective amount of an organic flocculating agent is added to the aqueous phase in order to precipitate essentially all the fluoropolymer particles.

7. The process as claimed in claim 6, wherein the flocculating agent is an organic cationic flocculating agent.

8. The process as claimed in claim 7, wherein the flocculating agent is added to the untreated or treated aqueous phase.

* * * * *

UNITED STATES PATENT AND TRADEMARK OFFICE
CERTIFICATE OF CORRECTION

PATENT NO. : 6,706,193 B1
DATED : March 16, 2004
INVENTOR(S) : Burkard, Georg

It is certified that error appears in the above-identified patent and that said Letters Patent is hereby corrected as shown below:

Column 3,
Lines 46-47, "didecyidimethylatnmonium" should be shown as
-- didecyldimethylammonium --

Column 6,
Line 7, table 4, "Total amount of waste water passed through" should be shown as
-- Total amount of waste water passed through [1] --

Signed and Sealed this

First Day of March, 2005

JON W. DUDAS
*Director of the United States Patent and Trademark Office*